(12) United States Patent
Hillebrand (10) Patent No.: US 11,352,617 B2
(45) Date of Patent: Jun. 7, 2022

(54) METHOD FOR ENRICHING BIOMOLECULES AND FOR REMOVING THE BIOMOLECULES FROM A BIOLOGICAL SAMPLE

(71) Applicant: IST Innuscreen GmbH, Berlin (DE)

(72) Inventor: Timo Hillebrand, Hoppegarten (DE)

(73) Assignee: IST INNUSCREEN GMBH, Berlin (DE)

(*) Notice: Subject to any disclaimer, the term of this patent is extended or adjusted under 35 U.S.C. 154(b) by 374 days.

(21) Appl. No.: 16/320,685

(22) PCT Filed: Jul. 25, 2016

(86) PCT No.: PCT/EP2016/067667
§ 371 (c)(1),
(2) Date: Jan. 25, 2019

(87) PCT Pub. No.: WO2018/019360
PCT Pub. Date: Feb. 1, 2018

(65) Prior Publication Data
US 2020/0181600 A1    Jun. 11, 2020

(51) Int. Cl.
*C12N 15/10* (2006.01)
*C07H 21/04* (2006.01)

(52) U.S. Cl.
CPC ............... *C12N 15/1013* (2013.01)

(58) Field of Classification Search
CPC .................................................. C12N 15/1013
USPC .......................................... 536/25; 435/239
See application file for complete search history.

(56) References Cited

U.S. PATENT DOCUMENTS

| | | | |
|---|---|---|---|
| 5,665,582 A * | 9/1997 | Kausch | C12N 15/1013 435/181 |
| 2010/0190240 A1* | 7/2010 | Jiang | C12N 15/1013 435/270 |
| 2011/0117628 A1 | 5/2011 | Hillebrand | |

FOREIGN PATENT DOCUMENTS

| | | |
|---|---|---|
| DE | 198 56 415 | 6/2001 |
| DE | 10 2008 023 297 | 6/2014 |
| DE | 10 2015 215894 | 9/2016 |
| EP | 2 261 231 | 12/2010 |
| WO | 2009/135936 | 11/2009 |
| WO | 2013/124863 | 8/2013 |

OTHER PUBLICATIONS

International Search Report dated Mar. 24, 2017 in PCT/EP2016/067667.
Written Opinion dated Mar. 24, 2017 in PCT/EP2016/067667.

* cited by examiner

*Primary Examiner* — Jeremy C Flinders
(74) *Attorney, Agent, or Firm* — Grüneberg and Myers PLLC (57) ABSTRACT

A method includes enriching biomolecules and removal of the biomolecules from a biological sample. In the presence of particles, an alginate solution and salts of divalent and/or polyvalent cations or an acid are added to a biological sample, and an alginate-gel-biomolecule-complex is formed on the particles. The complex is removed from the sample by separation of the particles, and from which subsequently the biomolecules or ingredients of the biomolecules are released. The biomolecules, which shall be enriched, include cell-free nucleic acids, viruses or subcellular microparticles.

10 Claims, 3 Drawing Sheets

Specification includes a Sequence Listing.

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: sense primer

<400> SEQUENCE: 1
cgccgccaac gcgcaggtct a                                              21

<210> SEQ ID NO 2
<211> LENGTH: 20
<212> TYPE: DNA
<213> ORGANISM: Artificial Sequence
<220> FEATURE:
<223> OTHER INFORMATION: antisense primer

<400> SEQUENCE: 2
agccgaacgc cgcagcctca                                                20

<210> SEQ ID NO 3
<211> LENGTH: 19
<212> TYPE: DNA
<213> ORGANISM: Artificial Sequence
<220> FEATURE:
<223> OTHER INFORMATION: Probe

<400> SEQUENCE: 3
cctcccctac ggccccggg                                                 19

<210> SEQ ID NO 4
<211> LENGTH: 24
<212> TYPE: DNA
<213> ORGANISM: 5' Noncoding Region of Yellow Fever Virus

<400> SEQUENCE: 4
gctaattgag gtgyattggt ctgc                                           24

<210> SEQ ID NO 5
<211> LENGTH: 21
<212> TYPE: DNA
<213> ORGANISM: 5' Noncoding Region of Yellow Fever Virus

<400> SEQUENCE: 5
ctgctaatcg ctcaamgaac g                                              21

<210> SEQ ID NO 6
<211> LENGTH: 24
<212> TYPE: DNA
<213> ORGANISM: 5' Noncoding Region of Yellow Fever Virus

<400> SEQUENCE: 6
atcgagttgc taggcaataa acac                                           24

METHOD FOR ENRICHING BIOMOLECULES AND FOR REMOVING THE BIOMOLECULES FROM A BIOLOGICAL SAMPLE

CROSS-REFERENCE TO RELATED APPLICATIONS

This application is a National Stage entry under § 371 of International Application No. PCT/EP2016/067667, filed on Jul. 25, 2016, which is incorporated in its entirety.

REFERENCE TO A SEQUENCE LISTING

The instant application contains a Sequence Listing which has been submitted electronically in ASCII format and is hereby incorporated by reference in its entirety. Said ASCII copy, created on Apr. 9, 2019, 9:23 AM, is named "2019-04-09-seq-list-as-filed.txt" and is 1,403 bytes in size.

BACKGROUND OF THE INVENTION

Field of the Invention

The subject matter of the invention is a simple method for enriching biomolecules and for removal (isolation) of the biomolecules from a sample for a subsequent analysis of said biomolecules and/or for further processing. The biomolecules, which shall be enriched, include cell-free nucleic acids, viruses or subcellular microparticles (for example exosomes). The method is an improved and a simpler method than the method described in the printed patent specification DE 10 2008 023 297 B4.

Discussion of the Background

It is known that so-called freely circulating nucleic acids, exosomes as well as also virus particles in the case of a viral infection are located in cell-free body fluids. All these different biomolecules are of great importance for the diagnosis of diseases. In particular, cell-free nucleic acids as well as exosomes play an increasingly important role here. All these biomolecules have also in common that they exist only in very low concentrations in body fluids. This makes their diagnostic use difficult. The only solution is to process larger sample volumes in order to have finally available a sufficient quantity of biomolecules. Important initial samples are, for example, body fluids such a blood plasma, serum or also urine.

At present, only a few methods exist which permit to enrich and/or isolate these biomolecules from a large volume sample and/or subsequently to use the enriched biomolecules for the extraction of nucleic acids.

Hence, for enriching exosomes from a biological sample, there is, for example, the application of ultracentrifugation techniques. Exosomes accumulate on the bottom of the reaction vessel in that case. Said method is bound to an ultracentrifuge, and moreover is time-consuming and unsuitable for routine diagnostics. Moreover, also the technique of ultrafiltration is used. This method as well is time-consuming and very expensive. Alternative methods consist of an immunoprecipitation of the exosomes by means of an immunoplate or by means of immunobeads. This type of enrichment of exosomes is time-consuming as well and due to the reagents to be used prone to failure as well as expensive. Furthermore, in this technology only 200 to 500 µl of a sample can be used. For the enrichment of viruses, ultracentrifugation techniques can also be used. Alternative methods consist of the precipitation of virus particles by means of polyethylene glycol/sodium chloride and a subsequent centrifugation (Yamamoto et al., Virology 40 (1970) 734; Morandi et al., J. Clin. Microbiol. 36 (1998) 1543-1538). Here, one uses several mixtures of PEG and sodium chloride, and mixes these reagents with the biological sample. Subsequently, the batch is incubated in cold for a longer period of time, and thereafter the virus (protein)— NaCl/PEG precipitates are obtained by centrifugation. These methods are complex as well and require a lot of time. Moreover, further processing of the precipitates for isolation of the viral nucleic acids is a problem. Often, the precipitates can hardly be dissolved again. This affects efficiency and quality of the nucleic acid isolation considerably. The patent specification DE 19856415 C2 describes a method using the known NaCl/PEG precipitation, wherein subsequently the isolation of the nucleic acids is realized in a manner known per se via the binding to a solid silicate phase. It does not become clear as to what extent said process differs from the sufficiently known method of the NaCl/PEG precipitation with the known problems. Moreover, this method as well requires cold incubation and twenty minutes of centrifugation. The process is supposed to permit isolation of viral nucleic acids from a sample of up to 10 ml. Another commercially available alternative, which shall permit treatment of up to 1 ml of a sample, is based on enriching viral nucleic acids by using a special detergent. Here, an initial incubation of the sample with a lysis reagent results in the lysis of the viruses. Subsequently, a "detergent nucleic acid complex" is formed. The batch is centrifuged and the pellet obtained is subsequently treated proteolytically, and the nucleic acid in turn is isolated in a manner known per se via the binding to a solid silicate phase. (QIAamp UltraSens Virus Handbook). Here as well, the problems with resuspension of the pellets are pointed out. Furthermore, the method also permits only processing of samples with a volume of 1 ml max.

For isolation of circulating, cell-free DNA from large volume samples it is proceeded in such a way that all buffer components, which are required for extraction, are scaled up. It is known to the person skilled in the art that this is associated with a huge amount of reagents as well as time.

It becomes also clear to the person skilled in the art that for different biomolecules (for example viruses or DNA or subcellular particles) always also different methods are required, when one wants to concentrate and/or purify the biomolecules from a sample.

An entirely new approach for the concentration of biomolecules from a biological sample and for subsequent extraction of nucleic acids is disclosed in the patent specification DE 10 2008 023 297 B4.

The method is based on the utilization of polysaccharide derivatives for complexing of the biomolecules contained in a sample. The polysaccharide derivatives are salts of polyuronic acids. Here, the so-called alginates of the alginic acids are particularly suitable. Alginates are structural elements in brown algae. Alginate is a polysaccharide which consists of 1.4 linked α-L guluronic acid (G) and β-D-mannuronic acid (M).

D-mannuron-   L-Guluron-
silure        silure

Alginsilure

It forms homopolymeric areas in which mannuronic acid or guluronic acid exists as a block.

Alginates are used in the food industry as well as in the pharmaceutical and cosmetics industry, for example, as a gelling agent in the food industry, as a finishing agent for textiles, for the production of photographic papers or in dental practices for the production of dental and jaw impressions.

The patent specification describes the use of the ability of alginates to gel in solutions with low calcium content, and to form so-called hydrogels. The cause of gelling is due to the storage of calcium ions into the zigzag structure of the GG-blocks. The zigzag structure of another alginate molecule then settles on said zone. Three-dimensional structures form as a result. The formation of gels also occurs combined with strong acids. Moreover, the gel structures formed can also be specifically destroyed again.

By using the formation of alginate gels, enrichment of biomolecules can occur in a simple and rapid manner, and subsequently the isolation of nucleic acids can be carried out.

The sequence of the process is described as follows:
1. mixing of an aqueous alginate solution with a liquid biological sample
2. addition of an aqueous solution which induces gel formation/pellet formation (for example, using a 1 M calcium chloride solution or a 1% hydrochloric solution)
3. mixing of the sample and short incubation at room temperature
4. centrifugation of the sample and removal of the supernatant
5. dissolving the pellet or gel piece and thus release of the biomolecules and, if required, subsequent direct isolation of DNA or RNA in a manner known per se.

The method disclosed in the patent specification is extremely efficient and permits to use also large volume samples in a rapid and simple manner for the enrichment of biomolecules.

But the method described has one great disadvantage. Automation of the process is difficult to perform. The reason for it is that the enrichment step must always occur by means of centrifugation. As it is known, integration of a centrifugation step into an automated process is not easy to implement, and moreover significantly increases cost expenditure for an automat.

SUMMARY OF THE INVENTION

Task of the Invention

It has been the task of the invention to eliminate the disadvantages of the known technical solutions.

Solution of the Task

The task has been solved in accordance with the features of the patent claims. The method according to the invention permits to enrich biomolecules (also from large volume samples), and to subsequently release the biomolecules or to isolate from them, if required, nucleic acids (DNA and RNA) and/or to release the nucleic acids.

The method permits to implement all necessary process steps in a simple and rapid manner into an automated process. Surprisingly, this can be carried out in a totally simple manner without a centrifugation step.

The method is based on the known process of adding an alginate solution and salts of divalent and/or polyvalent cations (for example, calcium, zinc or aluminium salts) or an acid to a biological liquid sample. But subsequently, enrichment of the biomolecules does not occur by means of a centrifugation step. Particles, preferably magnetic or paramagnetic particles, are added to the sample. It is unimportant here what kind of particles these are. Not only the size of the particles but also their functionalization is of minor importance. Thus, nanoparticles, microparticles or larger particles can be used. For a simple separation of the particles, magnetic particles are most appropriate. In that case, the particles are separated by means of a magnet, and the sample supernatant is removed. After removal of the sample supernatant, the biomolecules to be enriched (subcellular particles, viruses or nucleic acids) are entirely within a complex of alginate gel and magnetic and/or paramagnetic particles. Hence, this enrichment surprisingly took place without the centrifugation mentioned in the patent specification DE 10 2008 023 297 B4. Release of the complexed biomolecules can now take place by the fact that reagents are added, which destroy again the alginate gel structure, and thus release the complexed biomolecules. This can, for example, take place by means of a buffer solution, which contains a chelating agent (EDTA) or by means of the addition of a solution from trisodium citrate dihydrate. After the addition of these reagents, a short resuspending of the particles and an incubation takes pace. The incubation serves for dissolving the alginate gel structure and release of the biomolecules. Subsequently, the magnetic and/or paramagnetic particles are separated by applying a magnetic field. The resulting supernatant contains the biomolecules which can subsequently be worked up or analyzed.

As a result, the method does not need a centrifugation step and can be carried out in a very simple manner, and entirely automatically. Thus, it is possible for the first time to process also large sample sizes in an efficient and rapid manner.

The method according to the invention has still another advantage. In a special embodiment, the particles used for the separation can be selected in such a manner that they are able to bind nucleic acids. This means that the particles on the one hand serve for separation of the biomolecule-alginate-complex and subsequently also for extraction of ultrapure nucleic acids. This method is particularly important, when so-called circulating, cell-free nucleic acids shall be enriched from a cell-free sample, and subsequently isolated. For this purpose, an alginate solution and an aqueous solution containing salts of divalent and/or polyvalent cations (for example, calcium chloride or aluminium chloride) or a weak acid as well as paramagnetic or magnetic particles are added to the sample (serum, plasma, urine etc.). Said particles are selected such that under specific conditions they can bind nucleic acids. Such particles are known to the person skilled in the and are used in routine for the isolation of nucleic acids. After the addition of these components, the batch is briefly mixed and incubated for a few minutes at room temperature. Subsequently, the particles are separated by means of a magnet, and the sample supernatant is removed. After removal of the supernatant, a buffer is added to the particles (the alginate-gel-particle-complex) which buffer permits a destruction of the alginate-gel-complex. For this purpose, the particles are resuspended, and the batch is incubated for a few minutes. In this process, also further additives such as proteolytic enzymes etc. can be added to the buffer. The incubation can take place at room temperature or also at higher temperatures, preferably 50° C. up to 70° C. After release of the complexed, cell-free nucleic acid, the nucleic acid binds to the magnetic or paramagnetic particles. This may occur by the buffer used. Preferably, one increases the efficiency of binding of the DNA by the addition of a binding buffer. As a buffer, reagent combinations can be used which are known to the person skilled in the art from the patent specification DE 10 2008 023 297 B4. It is important that the first buffer permits destruction of the alginate gel structure and a subsequent binding of the released DNA, alone or in combination with an additional binding buffer.

It is also possible to use a binding buffer beside the lysis buffer which permits to achieve a selectivity with respect to the nucleic acids to be purified (size fractionation or separation of DNA and RNA). The further extraction process is known to the person skilled in the art. The nucleic acids bound to the particles are washed and the nucleic acids are finally removed from the particles by the addition of water or by the addition of a low salt buffer.

By means of the method according to the invention, thus also the entire process, starting with the enrichment of biomolecules up to final extraction of ultrapure nucleic acids can be carried out automatically. No more centrifugation step is required. This represents a considerable advantage compared with the method disclosed in the patent specification DE 10 2008 023 297 B4. Furthermore, by means of the method according to the invention, de facto any sample volume can be processed, and it is thus not limited to small volumes, and moreover it is easy to automate. The volumes of the liquid initial samples can be selected at random which permits a very broad application range. One can work, for example, with sample of 500 µl but also 10 µl. Thus, an extremely large application width exists.

The method according to the invention is also suitable for generally isolating nucleic acids from a sample. If the nucleic acids to be isolated do not exist as free nucleic acids, the sample can be lysed in a manner known per se. The nucleic acids released from the sample as a result are subsequently isolated in turn in accordance with the method according to the invention. Here as well, after dissolving of the alginate gel structure (which contains the enriched nucleic acid), a "traditional" purification of the nucleic acids can be carried out or one can use the solution obtained after dissolving the alginate gel structure by means of a basic low salt buffer directly for a PCR reaction.

The invention is subsequently explained more in detail by means of embodiments, wherein the embodiments do not constitute a limitation of the method according to the invention.

DETAILED DESCRIPTION OF THE INVENTION

Embodiment 1

Enrichment of cell-free DNA from a plasma sample of 1 ml. Proof of the necessary combination of alginate solution, reagent for formation of an alginate gel as well as particles separable by means of a magnetic field Initial sample for the enrichment had been human plasma. The plasma sample had been centrifuged again for 10 minutes prior to the application in order to remove still existing cells, if applicable. Further processing took place with the supernatant. Three different processes have been tested.

Sample 1: 30 µl of a 0.5% alginate solution were added to the sample and the batch was briefly mixed. Subsequently, 150 µl of a 1 molar calcium chloride solution were added as well as 50 µl of a magnetic particle suspension (MAG Suspension; Analytik Jena AG).

Sample 2: 30 µl of a 0.5% alginate solution were added to the sample and the batch was briefly mixed. Subsequently 50 µl of a magnetic particle suspension (MAG Suspension; Analytik Jena AG) were added.

Sample 3: 150 of a 1 molar calcium chloride solution were added to the sample and the batch was briefly mixed. Subsequently 50 µl of a magnetic particle suspension (MAG Suspension; Analytik Jena AG) were added.

The samples were then processed further as follows.

The batch was briefly mixed and incubated for 10 minutes. Subsequently, separation of the magnetic particles by means of a magnet took place. The supernatant was removed and the magnetic particles were washed with 1 ml water. After renewed separation of the magnetic particles, the supernatant was completely removed.

400 µl buffer (4 M guanidine thiocyanate, EDTA) as well as 20 µl proteinase K (20 mg/ml) were added to the magnetic particle-alginate-gel-DNA-complex and the batch was resuspended by means of a pipette. Subsequently, an incubation for 15 minutes at 70° C. took place.

This step served for destruction of the particle-alginate-gel-DNA-complex and thus the release of the complexed DNA. Subsequently, the addition of 400 µl of a binding buffer (isopropanol/triton X-100) and a renewed mixing of the particles as well as an incubation for 2 minutes took place. This step served for binding of the DNA to the particles. Subsequently, the magnetic particles were separated and the supernatant was discarded. Thereafter, the particles were washed with alcoholic wash buffers known to the person skilled in the art, and finally dried. In the last step, the bound DNA was detached from the particles by the addition of 50 µl $H_2O$, and transferred to a new reaction vessel.

The proof of enrichment and subsequent extraction of cell-free DNA took place by means of Real Time PCR. For this purpose, a human specific target sequence oestrogen receptor 1 has been amplified.

Protocol RealTime PCR for Amplification of the human specific Target Sequence (Oestrogen Receptor 1).

```
sense Primer
(5'- CGC CGC CAA CGC GCA GGT CTA-3')

antisense Primer
(5'- AGC CGA ACG CCG CAG CCT CA-3')

1 probe
(5'-FAM CCTCCCCTACGGCCCCGGG-BHQ1-3')
```

Reaction mixture
per sample:

| | |
|---|---|
| sense Primer (50 pmol/µl) | 0.1 µl |
| antisense Primer (50 pmol/µl) | 0.1 µl |
| probe (25 pmol/µl) | 0.1 µl |
| dNTP-Mix (12.5 mM) | 0.3 µl |
| 10X PCR buffer (MgCl$_2$ included) | 1.5 µl |
| Taq-DNA-Polymerase | 0.75 U |
| PCR-Grade H$_2$O | add 15 µl |

Amplification/Hybridization Conditions

| Step 1: | | |
|---|---|---|
| Denaturation | 95° C. | 120" |
| Step 2 | | |
| Amplification | 45 cycles | |
| | 95° C. | 4" |
| (measurement) | 65° C. | 45" |

Result PCR

Figure 1:
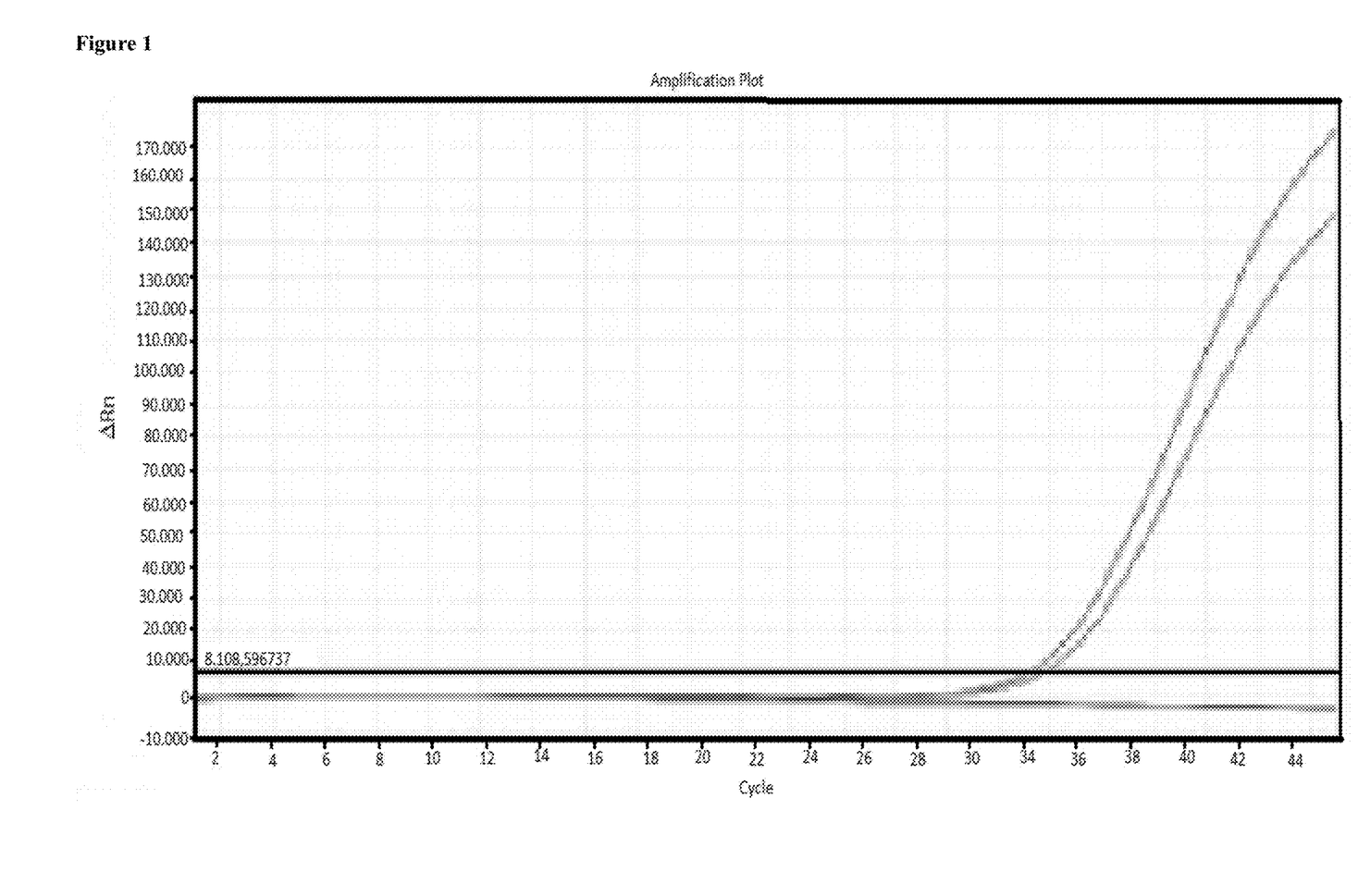
FIG. 1 depicts the result of PCR, showing that only the combination of alginate solution, reagent for the formation of an alginate gel as well as particles separable by means of a magnet field permits an enrichment and subsequent extraction of DNA.

The results in FIG. 1 show that only the combination of alginate solution, reagent for the formation of an alginate gel as well as particles separable by means of a magnet field permits an enrichment and subsequent extraction of DNA (black graphs). Thus, it is proven that the first step is the complexation of free DNA with the forming alginate gel, and that the added particles combine with this complex. Thus, by applying a magnet field, the particle-alginate-gel-DNA-complex can be separated. Hence, a centrifugation, as this is described in the patent specification DE 10 2008 023 297 B4, is not necessary.

Embodiment 2

Enrichment of cell-free DNA from a plasma sample of 1 ml as well as of 5 ml and subsequent extraction of DNA Human plasma had been the initial sample for enrichment. Prior to application, the plasma sample had been centrifuged again for 10 minutes in order to remove still existing cells, where applicable. Further processing took place with the supernatant.

The 1 ml sample has been treated as follows. 30 µl of a 0.5% alginate solution were added to the sample, and the batch was briefly mixed. Subsequently, 150 µl of a 1 molar calcium chloride solution were added as well as 50 µl of a magnetic particle suspension (MAG Suspension; Analytik Jena AG). The batch was briefly mixed and incubated for 10 minutes. Subsequently, separation of the magnetic particles by means of a magnet took place. The supernatant was removed, and the magnetic particles were washed with 1 ml water. After renewed separation of the magnetic particles, the supernatant was completely removed.

400 µl buffer (4 M guanidine thiocyanate, EDTA) as well as 20 µl proteinase K (20 mg/ml) were added to the magnetic particle-alginate-gel-DNA-complex, and the batch was resuspended by means of a pipette. Subsequently, an incubation for 15 minutes at 70° C. took place.

This step served for destruction of the particle-alginate-gel-DNA-complex, and thus the release of the complexed DNA. Subsequently, the addition of 400 µl of a binding buffer (isopropanol/triton X-100) and a renewed mixing of the particles as well as an incubation for 2 minutes took place. This step served for binding of the DNA to the particles. Subsequently, the magnetic particles were separated, and the supernatant was discarded. Thereafter, the particles were washed with alcoholic wash buffers known to the person skilled in the art, and finally dried. In the last step, the bound DNA was detached from the particles by the addition of 50 µl H$_2$O, and transferred to a new reaction vessel.

The 5 ml sample were treated as follows. The sample was transferred to a 15 ml reaction vessel. 150 µl of an 0.5% alginate solution were added to the sample and the batch was briefly mixed. Subsequently 600 µl of a 1 molar calcium chloride solution as well as 100 µl of a magnetic particle suspension (MAG Suspension; Analytik Jena AG) were added. The batch was briefly mixed and incubated for 10 minutes. Subsequently, separation of the magnetic particles by means of a magnet took place. The supernatant was removed and the magnetic particles were washed with 5 ml water. After renewed suspension of the magnetic particles, the supernatant was completely removed.

400 µl buffer (4 M guanidine thiocyanate, EDTA) as well as 20 µl proteinase K (20 mg/ml) were added to the magnetic particle-alginate-gel-DNA-complex, resuspended, and the batch was transferred by means of a pipette into an 1.5 ml reaction vessel. Subsequently, an incubation for 15 minutes at 70° C. took place.

This step served for destruction of the particle-alginate-gel-DNA-complex and thus the release of the complexed DNA. Subsequently, the addition of 400 µl of a binding buffer (isopropanol/triton X-100) and a renewed mixing of the particles as well as an incubation for 2 minutes took place. This step served for binding of the DNA to the particles. Subsequently, the magnetic particles were separated and the supernatant was discarded. Thereafter, the particles were washed with alcoholic wash buffers known to the person skilled in the art, and finally dried. In the last step, the bound DNA was detached from the particles by the addition of 50 µl H$_2$O, and transferred to a new reaction vessel.

The proof of enrichment and subsequent extraction of cell-free DNA took place by means of Real Time PCR. For this purpose, a human specific target sequence (oestrogen receptor 1) has been amplified.

Results Real Time PCR

Protocol Real Time PCR for amplification of human specific target sequence (oestrogen receptor 1). Protocol see example 1.

| Sample | Ct values |
|---|---|
| 1 ml sample (red graph) | 35/34.95 |
| 5 ml sample (black graph) | 32.25/32.30 |

Figure 2:
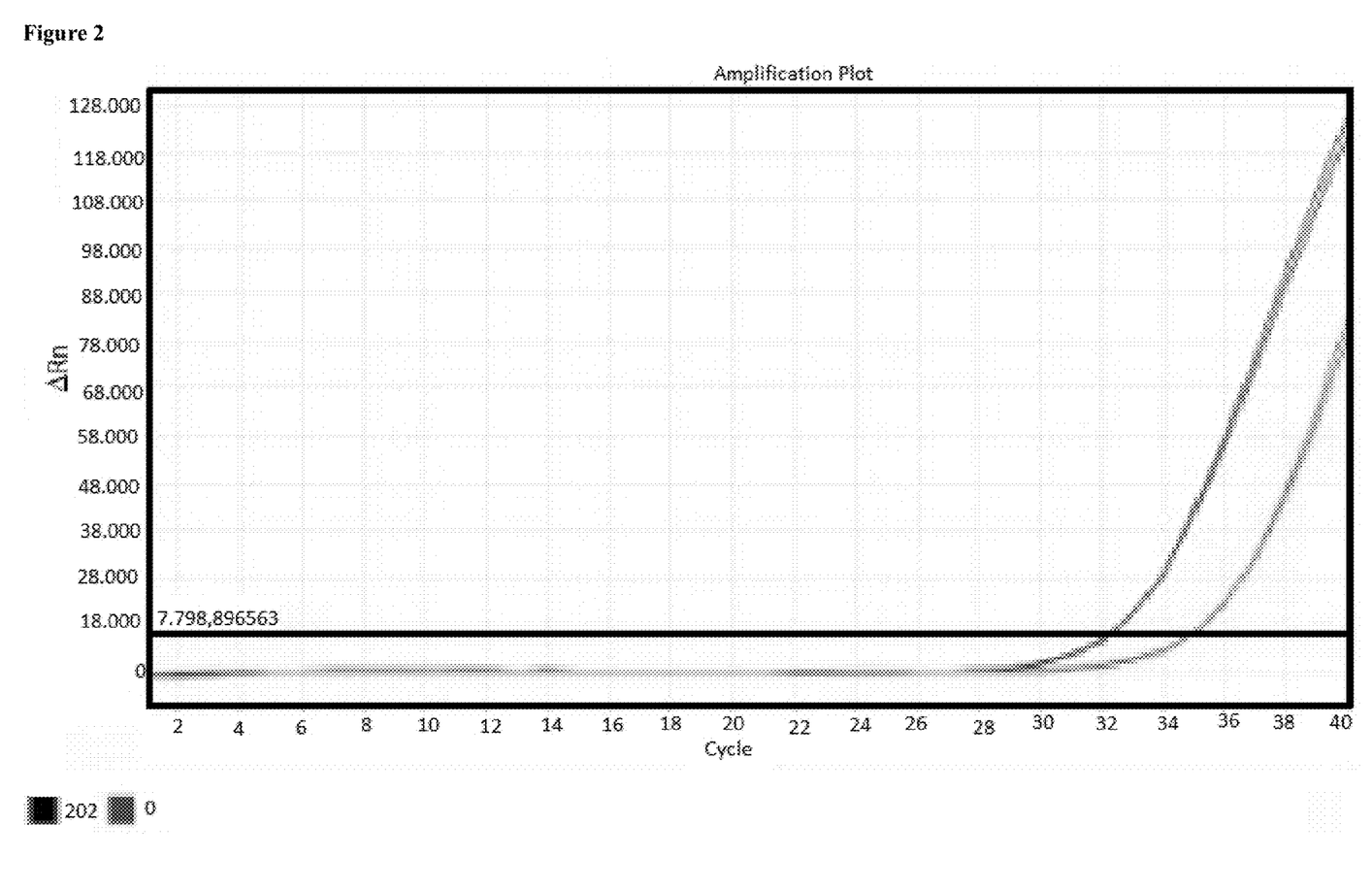
FIG. 2 depicts the result of real time PCR, showing that 5 ml sample DNA was more enriched and subsequently isolated than 1 ml sample.

As the results in FIG. 2 show, from the 5 ml sample more DNA is enriched and subsequently isolated than from the 1 ml sample. Thus, the method according to the invention is suitable also for the enrichment and extraction cell-free of DNA from large volume samples.

Embodiment 3

Enrichment of genomic DNA from an aqueous solution (1 ml) and direct release of the genomic DNA without further DNA extraction. Comparison of the method according to the invention with the method from the patent specification DE 10 2008 023 297 B4

The initial sample for enrichment was an aqueous solution which contained genomic DNA. Enrichment occurred by means of the method from the patent specification DE 10 2008 023 297 B4 as well as by means of the method according to the invention without a centrifugation step. For the method from the patent specification, the commercial product PME free-circulating DNA Extraction Kit (Analytik Jena AG) has been used. The method according to the invention was carried out as follows.

30 µl of a 0.5% alginate solution were added to the sample, and the batch was briefly mixed. Subsequently, 150 µl of a 1 molar calcium chloride solution were added as well as 50 µl of a magnetic particle suspension (MAG Suspension; Analytik Jena AG). The batch was briefly mixed and incubated for 5 minutes. Subsequently, separation of the magnetic particles by means of a magnet took place. The supernatant was removed, and the magnetic particles were washed with 1 ml water. After renewed separation of the magnetic particles, the supernatant was completely removed. The magnetic particle-alginate-gel-DNA-complex was subsequently destroyed in order to release the DNA. For this purpose, 50 µl of a 50 mM sodium citrate solution were added to the particles, and the batch was resuspended by means of a pipette. After a short incubation, the magnetic particles were separated, and the supernatant was transferred to a new vessel, and subsequently 50 µl water were added. The analysis as to whether the genomic DNA of the sample was enriched also without centrifugation, took place on an agarose gel. As it is shown by the gel-electrophoretic representation, the genomic DNA from the 1 ml sample could be concentrated by means of both methods. In this context, the method according to the invention distinguishes itself by its simplicity because no more centrifugation steps were required.

Figure 3:
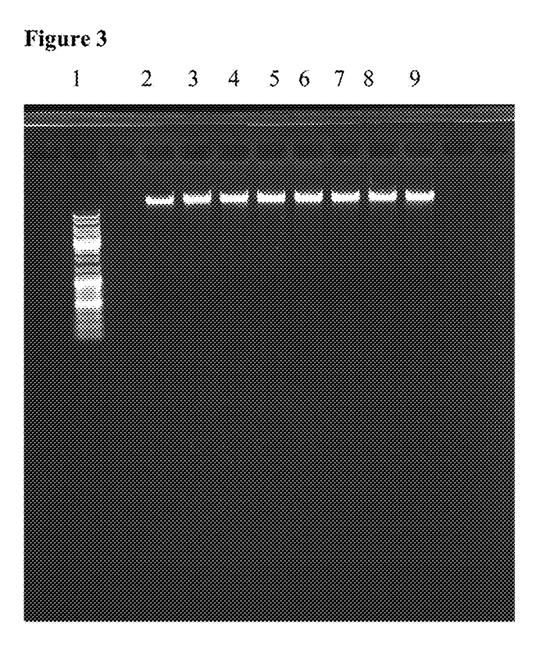
FIG. 3 depicts the gel-electrophoretic representation of the concentrated DNA.

FIG. 3 shows the gel-electrophoretic representation of the concentrated DNA by means of both methods, wherein No. 1 shows the 1-DNA ladder, Nos. 2 to 5 show the concentrated genomic DNA by means of the method from patent specification DE 10 2008 023 297 and Nos. 6 to 9 show the concentrated genomic DNA by means of the method according to the invention.

Embodiment 4

Enrichment of Viruses and subsequent Extraction of the viral Nucleic Acid

Human plasma was the initial sample for the enrichment. Inactivated yellow fever virus was added to the plasma sample. For enrichment of the viruses, 1 ml sample was used. The 1 ml sample was treated as follows. 30 µl of a 0.5% alginate solution were added to the sample, and the batch was briefly mixed. Subsequently, 150 µl of a 1 molar calcium chloride solution were added as well as 50 µl of a magnetic particle suspension (MAG Suspension; Analytik Jena AG). The batch was briefly mixed, and incubated for 10 minutes. Subsequently, separation of the magnetic particles by means of a magnet took place. The supernatant was removed, and the magnetic particles were washed with 1 ml water. After renewed separation of the magnetic particles, the supernatant was completely removed.

400 µl buffer (4 M guanidine thiocyanate, EDTA) as well as 20 µl proteinase K (20 mg/ml) were added to the magnetic particle-alginate-gel-DNA-complex, and the batch was resuspended by means of a pipette. Subsequently, an incubation for 15 minutes at 60° C. took place.

This step served for destruction of the particle-alginate-gel-virus-complex and thus the release of the complexed viruses and destruction for release of the viral nucleic acid (viral RNA). Subsequently, the addition of 400 µl of a binding buffer (guanidine thiocyanate/isopropanol/triton X-100) and a renewed mixing of the particles as well as an incubation for 2 minutes took place. This step served for binding of the viral RNA to the particles. Subsequently, the magnetic particles were separated and the supernatant was discarded. Thereafter, the particles were washed with alcoholic wash buffers known to the person skilled in the art, and finally dried. In the last step, the bound DNA was detached from the particles by the addition of 50 µl $H_2O$, and transferred to a new reaction vessel.

The proof of enrichment of the virus particles, and the subsequent extraction of the viral RNA took place by means of a yellow fever virus specific Real Time PCR.

Results Real Time PCR

Protocol Real Time PCR for amplification of the 5' Noncoding Region of Yellow Fever Virus

```
Y case F:
(5'-GCTAATTGAGGTGYATTGGTCTGC-3')

Y case R
(5'-CTGCTAATCGCTCAAMGAACG-3')

Y case P
(5'-FAM-ATCGAGTTGCTAGGCAATAAACAC-BHQ1-3')
```

Reaction Batch
per sample:

| | |
|---|---|
| Y case F (50 pmol/µl) | 0.1 µl |
| Y case R (50 pmol/µl) | 0.1 µl |
| Y case P (25 pmol/µl) | 0.1 µl |
| dNTP-Mix (12.5 mM) | 0,3 µl |
| 10X PCR buffer ($MgCl_2$ included) | 1.5 µl |
| Taq-DNA-Polymerase | 0.75 U |
| PCR-Grade $H_2O$ | add up to 15 µl |

Amplification/Hybridization Conditions

| Step 1: | | |
|---|---|---|
| Denaturation | 95° C. | 120 sec |
| Step 2 | | |
| Amplification | 45 cycles | |
| | 95° C. | 4 sec |
| (measurement) | 65° C. | 45 sec |

Results PCR

| Sample | Ct values |
|---|---|
| 1 ml sample (blue) | 28.8/28.9 |

Figure 4:
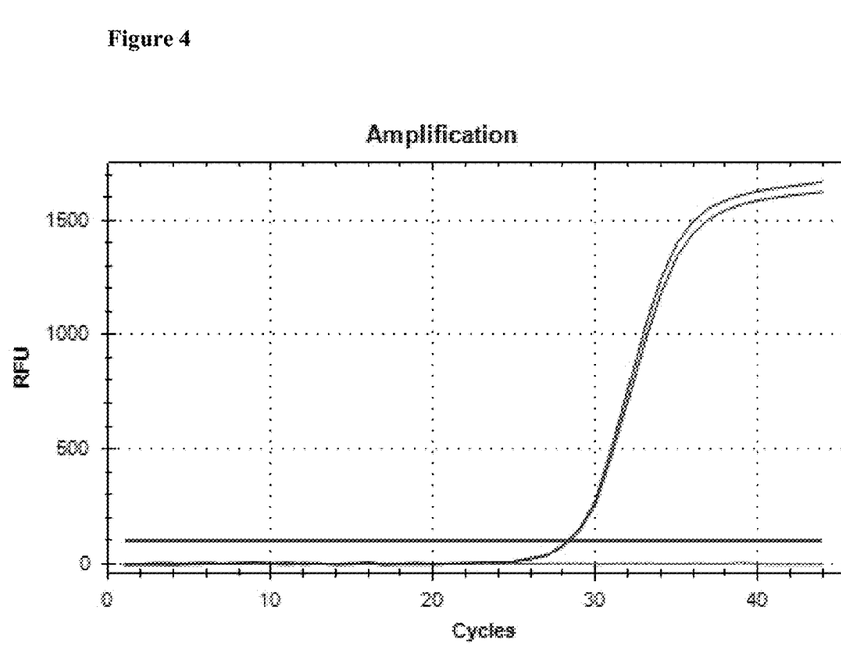
FIG. 4 depicts the result of PCR, showing that viruses are also enriched.

In FIG. 4 it has been shown that also viruses are enriched, and subsequently the viral nucleic acid can be extracted.

The invention claimed is:

1. A method for enriching a biomolecule and for removal of the biomolecule from a biological sample, said method comprising:
adding, in the presence of a magnetic particle, an alginate solution and a salt of a divalent cation and/or a polyvalent cation or an acid to the biological sample, wherein an alginate-gel-biomolecule-complex is formed on the magnetic particle, wherein the biomolecule is selected from the group consisting of cell-free nucleic acids, viruses, subcellular microparticles, and mixtures thereof,
removing said complex from the biological sample by separation of the magnetic particle, and
subsequently releasing the biomolecules or an ingredient of the biomolecule from the alginate-gel-biomolecule-complex.

2. The method according to claim 1, wherein calcium, zinc, aluminum, or combinations thereof are used as the salt of the divalent cation and/or the polyvalent cation.

3. The method according to claim 1, wherein separation of the magnetic particle from the alginate-gel-biomolecule-complex takes place via a magnet.

4. The method according to claim 1, wherein the release of the biomolecule takes place by dissolving of the alginate-gel-biomolecule-complex, which is located on the magnetic particle, wherein the magnetic particle and the biomolecule are released.

5. The method according to claim 4, wherein dissolving of the alginate-gel-biomolecule-complex takes place by trisodium citrate dihydrate or by a chelating agent.

6. The method according to claim 4, wherein after dissolving of the alginate-gel-biomolecule-complex located on the magnetic particle, resuspending of the magnetic particle and an incubation takes place, and the magnetic particle is separated.

7. The method according to claim 6, wherein the biomolecule is selected from the group consisting of cell-free nucleic acids, and wherein the magnetic particle, on which the alginate-gel-nucleic acid-complex has formed, after dissolving of the alginate-gel-nucleic acid-complex, at the same time binds the cell-free nucleic acid released from the alginate-gel-nucleic acid-complex.

8. The method according to claim 7, further comprising:
    after dissolving of the alginate-gel-nucleic acid-complex and resuspension of the magnetic particle, adding a binding buffer for binding the cell-free nucleic acids to the magnetic particles, and isolating the cell-free nucleic acids.

9. The method according to claim 5, wherein the chelating agent is EDTA.

10. The method according to claim 1, wherein the biological sample is at least one member selected from the group consisting of serum, plasma, and urine.

* * * * *